United States Patent [19]

Musco et al.

[11] Patent Number: 4,857,101
[45] Date of Patent: Aug. 15, 1989

[54] METHOD OF SELECTIVELY CONTROLLING WEEDS IN CROPS OF CEREALS

[75] Inventors: Vincent A. Musco, Southampton, Pa.; Donald E. Kelley, Germantown, Tenn.; Carl O. Hansen, Fort Washington, Pa.

[73] Assignee: Rohm and Haas Company, Philadelphia, Pa.

[21] Appl. No.: 929,225

[22] Filed: Nov. 19, 1986

Related U.S. Application Data

[63] Continuation-in-part of Ser. No. 806,148, Dec. 6, 1985.

[51] Int. Cl.$^4$ ............................................. A01N 43/40
[52] U.S. Cl. ............................................. 71/94; 71/88
[58] Field of Search ............................................. 71/94

[56] References Cited

U.S. PATENT DOCUMENTS

| | | | |
|---|---|---|---|
| 4,397,680 | 8/1983 | Böhner et al. | 71/94 |
| 4,447,259 | 5/1984 | Ohyama et al. | 71/94 |
| 4,531,969 | 7/1985 | Nestler et al. | 71/108 |
| 4,564,381 | 1/1986 | Bieringer et al. | 71/94 |

FOREIGN PATENT DOCUMENTS 1177272  11/1984  Canada ............................................. 71/94

*Primary Examiner*—Glennon H. Hollrah
*Attorney, Agent, or Firm*—Barbara V. Maurer; Polly E. Ramstad

[57] ABSTRACT

Method for selectively controlling growth of undesirable monocotyledonous plants in an area containing growing undesirable monocotyledonous plants and an established cereal crop which comprises applying to said area an N-[2-(4(3,5-dichloro-2-pyridyloxy)phenoxy)propionyl]-(optionally alkyl substituted) isoxazolidine as described herein at a rate of application which controls growth of said undesirable plants and which does not significantly affect growth of said established cereal crop.

14 Claims, No Drawings

METHOD OF SELECTIVELY CONTROLLING WEEDS IN CROPS OF CEREALS

This application is a continuation-in-part of pending application Ser. No. 806,148, filed Dec. 6, 1985.

BACKGROUND OF THE INVENTION

This invention relates to a method for selectively controlling growth of undesirable plants in an area containing growing undesirable plants and an established cereal crop which comprises applying to said area N-[2-(4(3,5-dichloro-2-pyridyloxy)phenoxy)propionyl]-(optionally alkyl substituted) isoxazolidine as described herein at a rate of application which controls growth of said undesirable plants and which does not significantly affect growth of said established cereal crop.

During the past years, there has been an intensified search for selective herbicides. While various useful substances have been developed, there is still need for agents which have a better balance of properties or which exhibit special properties. Some compounds are highly toxic to all types of plants and thus lack the selectivity and differential characteristics which are necessary for many applications. For example, a herbicide will exhibit excellent activity against undesirable grassy weeds. Frequently, because of this activity such a herbicide also elicits a phytotoxic response in desirable grass plants. In meeting the need for a selective herbicide having excellent safety toward desired plants, the present invention provides a significant advance.

From U.S. Pat. No. 4,447,259, it is known that 2-(substituted-phenoxy)propionic acid derivatives having the formula

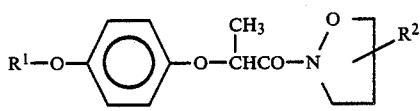

where

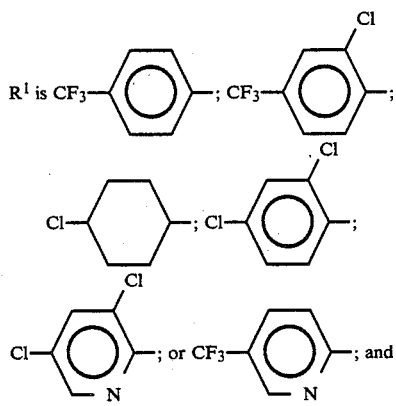

$R^2$ is hydrogen or lower alkyl; are herbicidally active compounds against grasses. Specifically disclosed weed species against which those compounds were tested are crabgrass (*Digitaria adscendens*), barnyardgrass (*Echinochloa crus-galli*), water foxtail (*Alopecurus aequalis*), annual bluegrass (*Poa annua*), green foxtail (*Setaria viridis*), common purslane (*Portulaca oleracea*), and common lambsquarters (*Chenopodium album*). The disclosed compounds were evaluated for their phytotoxity to broad leaved crop plants including soya bean, small red bean, sugar beet, radish and tomato. Significantly, the compounds disclosed in U.S. Pat. No. 4,447,259 patent along with certain compounds disclosed in relevant references cited therein, were evaluated on and found phytotoxic to wheat, the only cereal crop tested.

In evaluating the herbicidal activity of N-[2-(4(3,5-dichloro-2-pyridyloxy)phenoxy)propionyl] isoxazolidine, it has unexpectedly been found said compounds can be applied postemergence to cereal crops such as wheat, barley and rice, particularly wheat and rice, with substantially no phytotoxic effect while still providing excellent control of undesirable annual grasses, particularly wild oats, barnyardgrass, signalgrass, sprangletop, ryegrass and foxtails.

SUMMARY OF THE INVENTION

In accordance with the present invention there is provided a method for selectively controlling growth of undesirable plants in an area containing growing undesirable plants and an established cereal crop which comprises applying to said area a compound having the formula

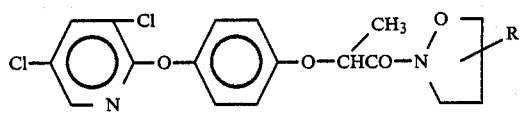

wherein R is hydrogen or lower ($C_1$–$C_4$)alkyl at a rate of application which controls growth of said undesirable plants and which does not significantly affect growth of said established cereal crop.

DETAILED DESCRIPTION OF THE INVENTION

This invention relates to a method for selectively controlling growth of undesirable plants in an area containing growing undesirable plants and an established cereal crop which comprises applying to said area a compound having the formula

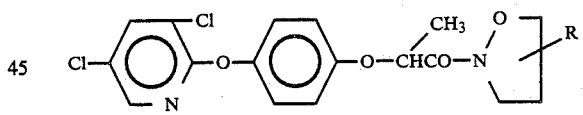

where R is hydrogen or lower ($C_1$–$C_4$)alkyl; at a rate of application which controls growth of said undesirable plants and which does not significantly affect growth of said established cereal crop.

Because of their activity and selectivity, the preferred N-[2-(4(3,5-dichloro-2-pyridyloxy)phenoxy)propionyl]-(optionally alkyl substituted) isoxazolidines described above for use in the present invention are those where R is hydrogen or methyl. Because of the activity and selectivity, most preferred N-[2-(4(3,5-dicloro-2-pyridyloxy)phenoxy)propionyl]-(optionally alkyl substituted) isoxazolidine described above for use in the present invention is where R is hydrogen.

The present invention contemplates treating an area under cultivation (i.e., a sown cereal crop) with a herbicidally effective amount of an N-[2-(4(3,5-dichloro-2-pyridyloxy)phenoxy)propionyl]-(optionally alkyl substituted) isoxazolidine as defined above at a rate of application which controls growth of said undesirable plants and which does not significantly affect growth of said cereal crop. The terms "control" and "herbicidal" are used interchangeably and as employed in the specification and claims of this application are to be construed as any means which adversely affects the existence or growth of the target (i.e., undesirable) plants. Such means can comprise a complete killing action, eradication, arresting in growth, inhibition, reducing in number or any combination thereof. By "herbicidally effective amount" is meant that dosage of active substance sufficient to exert "control" of undesirable plants. The term "contacting" as employed in the specification and claims of this application is to be construed as applying to such undesirable plants growing in an area of land under cultivation (i.e., a sown cereal crop) the active compound alone or as a constituent of a composition or formulation.

The N-[2-4(3,5-dichloro-2-pyridyloxy)phenoxy)propionyl]-(optionally alkyl substituted) isoxazolidines described herein are prepared as described in U.S. Pat. No. 4,447,259 which is incorporated herein and made a part hereof by reference.

In general, for the control of undesirable plants post-emergence in an area of land under cultivation (i.e., a sown cereal crop), the compound may be used at a dosage corresponding from about 0.01 to about 0.5 pounds of the active substance per acre and from about 0.05 to about 0.25 pounds per acre of the active substance is preferred. The exact amount of dosage for a given situation can be routinely determined and depends on a variety of factors, for example, the substance used, the kind of undesired plant, the formulation used, the state of the cereal crop and the prevailing weather conditions.

For practical applications, the N-[2-(4(3,5-dichloro-2-pyridyloxy)phenoxy)propionyl]-(optionally alkyl substituted) isoxazolidines described are utilized in the form of compositions of formulations. In these compositions and formulations, the active substances or substances are mixed with conventional inert agronomically acceptable (i.e., plant compatible and/or pesticidally inert) diluents or extenders such as solid carrier material or liquid carrier material, of the type usable in conventional compositions or formulations. By agronomically acceptable carrier is meant any substance which can be used to dissolve, disperse or diffuse the active ingredient in the composition without impairing the active ingredient's effectiveness and which by itself has no significant detrimental effect on the soil, equipment, desirable plants or agronomic environment. If desired, conventional adjuvants such as surfactants, stabilizers, antifoam agents and antidrift agents may also be added in accordance with agricultural practices. Examples of adjuvants which are commonly used in the art can be found in the John W. McCutcheon, Inc. publication "Detergents and Emulsifiers Annual."

Examples of compositions and formulations are aqueous solutions and dispersions, oily solutions and oil dispersion, dusting powders, wettable powders, emulsifiable concentrates, flowables, invert emulsions and aerosol compositions.

Wettable powders, flowables and emulsifiable concentrates are concentrated preparations which are diluted with water before or during use.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cottonseed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, isophorone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates. The following may be chiefly considered for use as conventional carrier vehicle assistants: emulsifying agents, such as cationic and/or nonionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolystates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers such as gum arabic, polyvinyl alcohol and polyvinyl acetate, can be used in the formulations.

The active compounds may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions and powders, which are thus ready for use.

The active compounds can be applied as sprays by methods commonly employed, such as conventional highgallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form average particle size of from about 50 to about 100 microns or less) using airplane crop spraying techniques. Typically only a few quarts per acre are needed and often amounts up to about 0.01 to one pound/acre, preferably about 0.02 to one-half pound/acre are sufficient. With ultra-low-volume, it is possible to use highly concentrated liquid compositions with said liquid carrier vehicles containing from about 20 to about 95% by weight of the active compound.

These formulations or compositions are applied in the usual manner, for instance by spraying, atomizing, vaporizing, dusting, watering, squirting, sprinkling and the like.

It will be realized, of course, that the concentration of the particular active compound utilized in admixture with the carrier vehicle will depend upon such factors as the type of equipment employed, method of application, area to be treated, types of weeds to be controlled and degree of infestation. Therefore, in special cases it is possible to go above or below the aforementioned concentration ranges.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and similar substances. Alternatively organic carrier materials such as, for example, ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance optionally dissolved in a volatile solvent such as acetone, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products. In the case of flowables, a liquid inert carrier such as water is also included.

To produce emulsifiable concentrates the active compound is dissolved or finely divided in a suitable solvent which preferably is poorly miscible with water, an emulifier being added to the resulting solution. Examples of suitable solvents are xylene, toluene, highboiling aromatic petroleum distillates, for example solvent naphtha, distilled tar oil and mixtures of these liquids. Examples of suitable emulsifers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight depending upon toxicant solubility. A suitable liquid highly concentrated primary composition other than an emulsifiable concentrate is a solution of the active substance in a liquid which is readily miscible with water, for example, acetone, to which solution a dispersant and, as the case may be, a wetting agent are added. When such a primary composition is diluted with water shortly before or during the spraying operation an aqueous dispersion of the active substance is obtained.

In addition to the aforementioned ingredients, the preparations according to the invention may also contain other substances commonly used in preparations of this kind.

For example, a lubricant, such as calcium stearate or magnesium stearate, may be added to a wettable powder or to a mixture to be granulated. Furthermore, there may, for example, be added "adhesives" such as polyvinylalcohol cellulose derivatives or other colloidal materials, such as casein, to improve the adherence of this herbicide.

Test results obtained by postemergence application of N-[2-(4(3,5-dichloro-2-pyridyloxy)phenoxy)propionyl] isoxazolidine are reported below to demonstrate these compounds, surprisingly, can be applied postemergence to cereal crops with substantially no phytotoxic effect while still providing excellent control of undesirable monocotyledonous and dicotyledonous plants, particularly annual grasses.

The following test procedure was employed. Field evaluations were conducted on one or more of the following plants:

| | Monocots | |
|---|---|---|
| Code Symbol | Common Name | Latin Name |
| BAR | Barley | Hordeum sativum |
| RIC | Rice | Oryza sativum |
| WHE | Wheat | Triticum spp. |
| AV FA | Wild Oats | Avena fatua |
| BR PL | Signalgrass | Brachiaria platyphylla |
| CY ES | Yellow Nutsedge | Cyperus esculentus |
| EC CR | Barnyardgrass | Echinochloa crus-galli |
| LE PA | Sprangletop | Leptochloa spp. |
| LO MU | Ryegrass | Lolium multifolrum |
| PA DI | Fall Panicum | Panicum dichotomiflorum |
| SE FA | Giant Foxtail | Setaria faberi |

| | Dicots | |
|---|---|---|
| Code Symbol | Common Name | Latin Name |
| AB TH | Velvetleaf | Abutilon theophrasti |
| AM AR | Ragweed | Ambrosia artemisiifolia |
| FA TA | Buckwheat | Fagopyrum faberi |
| CH AL | Lambsquarter | Chenopodium album |
| DA ST | Jimsonweed | Datura stramonium |
| PO PA | Purslane | Polygonum pennsylvanicum |
| ST ME | Chickweed | Stellaria media |

Field tests are conducted by applying treatments on individual plots usually measuring six to seven feet in width and fifteen to twenty feet in length. Each test is replicated two or four times. The test species are either still providing excellent control of undesirable monocotyledonous and dicotyledonous plants, particularly annual grasses.

The following test procedure was employed. Field evaluations were conducted on one or more of the following plants:

| | Monocots | |
|---|---|---|
| Code Symbol | Common Name | Latin Name |
| BAR | Barley | Hordeum sativum |
| RIC | Rice | Oryza sativum |
| WHE | Wheat | Triticum spp. |
| AV FA | Wild Oats | Avena fatua |
| BR PL | Signalgrass | Brachiaria platyphylla |
| CY ES | Yellow Nutsedge | Cyperus esculentus |
| EC CR | Barnyardgrass | Echinochloa crus-galli |
| LE PA | Sprangletop | Leptochloa spp. |
| LO MU | Ryegrass | Lolium multifolrum |
| PA DI | Fall Panicum | Panicum dichotomiflorum |
| SE FA | Giant Foxtail | Setaria faberi |

| | Dicots | |
|---|---|---|
| Code Symbol | Common Name | Latin Name |

| | | |
|---|---|---|
| AB TH | Velvetleaf | *Abutilon theophrasti* |
| AM AR | Ragweed | *Ambrosia artemisiifolia* |
| FA TA | Buckwheat | *Fagopyrum faberi* |
| CH AL | Lambsquarter | *Chenopodium album* |
| DA ST | Jimsonweed | *Datura stramonium* |
| PO PA | Purslane | *Polygonum pennsylvanicum* |
| ST ME | Chickweed | *Stellaria media* |

Field tests are conducted by applying treatments on individual plots usually measuring six to seven feet in width and fifteen to twenty feet in length. Each test is replicated two or four times. The test species are either planted into the plots or are found to be indigenous in the test area. A minimum of five plants per square meter are necessary for evaluation results on a given species to be reported. The application equipment is comprised of a series of spray nozzles that are spaced twenty inches apart and are mounted on a straight bar that is placed horizontal to the ground. The nozzles are designed to emit a flat fan spray pattern. Application is made by moving the nozzles across the plots at a constant speed and constant height above the spray target, such that the plots are sprayed uniformly. The rate of application of individual treatments is determined by varying the concentration of the spray solution, which is delivered at the rate of 20 to 30 gallons per acre.

The spray solution is prepared by mixing a measured amount of formulated test material into water, which is the spray carrier. The test material is formulated in an agronomically acceptable formulation such as a wettable powder, emulsifiable concentrate, flowable water soluble concentrate or dispersible granular. The formulated material when mixed with the water forms either a solution or a sprayable suspension. In some treatments, spray tank additives such as but not limited to surfactants or spray oils are added to the spray tank mixture.

Observations can be made from about three days after treatment to about thirty-five days after treatment depending upon how rapidly plants show symptoms of injury. Typically, observation times are predicated upon greenhouse evaluation results. The herbicidal effectiveness and crop injury are recorded as percent weed control and percent crop injury on a scale of 0–100 in which 0 equals no activity and 100 equals total kill.

The compound to be evaluated was formulated as an emulsifiable concentrate having the following composition (all amounts are percent by weight unless otherwise indicated):

| Wheat and Barley | |
|---|---|
| Toxicant and toxicant impurities | 6.5% |
| Triton ® AG-861 (emulsifier) anhydrous blend of alkyl polyether alcohols and organic sulfonates | 8.4% |
| Triton ® X-190 (emulsifier) anhydrous blend of alkyl polyether alcohols and organic sulfonates | 3.6% |
| Cyclohexanone (solvent) | 38.2% |
| Xylene (solvent) | 38.3% |
| Dimethylformamide (DMF) (solvent) | 5.0% |
| Rice | |
| Toxicant and toxicant impurities | 6.5% |
| Toximul R-HF (surfactant) blend of calcium dodecylbenzenesulfonate and alkyl aryl ethoxylate | 1.2% |
| Toximul S (surfactant) blend of calcium dodecylbenzene sulfonate and alkyl aryl ethyoxylate | 10.8% |
| Cyclohexanone (solvent) | 38.2% |
| Getty H-400 (solvent) blend of xylene and alkyl benzene | 38.3% |
| Dimethylformamide (DMF) (solvent) | 5.0% |

The emulsifiable concentrate formulation is then diluted with water to obtain the rate of application specified in Tables II to V and sprayed over the plots. In the rice tests the fields were flooded 1 to 10 days after application of the formulation.

In some treatments, Rigo oil or Agridex oil, commercially available concentrated crop oils containing about 83%, by weight, refined petroleum oil and 17%, by weight, surfactant was added to the spray tank at about 0.25%, volume by volume, prior to application as an adjuvant.

Evaluations were conducted on the compounds shown below in Table I. The results of these evaluations are shown below in Tables II and V.

TABLE I

| Example | Compound |
|---|---|
| A | 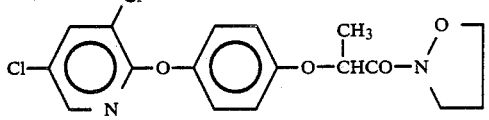 |

TABLE II

Percent Crop Injury and Weed Control[1]

| Example | Application Rate (lb./A) | BAR | WHE | AB TH | AM AR | FA TA | AV FA | CY ES | LO MU |
|---|---|---|---|---|---|---|---|---|---|
| A | 0.25 | 10 | 5 | 23 | 8 | 0 | 98 | 0 | 98 |
| | 0.5 | 67 | 47 | 30 | 10 | 0 | 100 | 0 | 100 |
| | 1.0 | 85 | 78 | 22 | 0 | 0 | 100 | 0 | 100 |
| A plus Oil | 0.25 | 43 | 25 | 18 | 8 | 0 | 100 | 0 | 100 |

[1]Plants were in the 3–5 leaf stage at application.

TABLE III

| | | Percent Crop Injury and Weed Control[1] | | | | | | | | | |
|---|---|---|---|---|---|---|---|---|---|---|---|
| | | | | Test Species | | | | | | | |
| Example | Application Rate (lb./A) | BAR | WHE | AB TH | AM AR | CH AL | FA TA | AV FA | LO MU | SE FA |
| A | 0.06 | 0 | 7 | 12 | 5 | 33 | 7 | 53 | 40 | 17 |
| | 0.12 | 12 | 10 | 23 | 13 | 32 | 7 | 73 | 70 | 57 |
| | 0.25 | 15 | 17 | 17 | 0 | 20 | 7 | 93 | 97 | 63 |
| A plus Oil | 0.03 | 10 | 8 | 13 | 15 | 28 | 7 | 67 | 55 | 32 |
| | 0.06 | 5 | 20 | 20 | 28 | 30 | 0 | 77 | 62 | 60 |
| | 0.12 | 5 | 8 | 18 | 12 | 12 | 3 | 92 | 88 | 47 |

[1]Plants were in the 4–6 leaf stage at application.

TABLE IV

| | | Percent Annual Grass Weed Control | | |
|---|---|---|---|---|
| | | Test Species | | |
| Example | Application Rate (lb./A) | BR PL[1] | EC CR[2] | LE PA[3] |
| A | 0.06 | 64 | 70 | 50 |
| A plus Oil | 0.03 | 62 | 44 | 50 |
| | 0.06 | 74 | 46 | 75 |
| | 0.12 | 82 | 84 | 97 |

[1]Average of evaluations from 4 trials on 4–6 leaf grass taken 21–30 days after application.
[2]Average of evaluations from 3 trials on 4–6 leaf grass taken 21 days after application.
[3]Average of evaluations from 2 trials on 2–3 leaf grass taken 21–30 days after application.

TABLE V

| | | Percent Rice Crop Injury | | | |
|---|---|---|---|---|---|
| | | Percent Injury[1] | | | |
| | | 1–3 Leaf[2] | | 4–6 Leaf | |
| Example | Application Rate (lb./A) | 7-Day[3] | 21-Day | 7-Day | 30-Day |
| A | 0.06 | 3 | 6 | 4 | 3 |
| A plus Oil | 0.06 | 5 | 6 | 4 | 0 |
| | 0.12 | 9 | 12 | 4 | 5 |

[1]Visual injury symptoms noted in the form of leaf yellowing and necrosis.
[2]Size of rice at application.
[3]Denotes no. of days evaluation follows application.

We claim:

1. A method for selectively controlling growth of undesirable monocotyledonous plants in an area containing growing undesirable monocotyledonous plants and an established wheat, barley or rice crop which comprises applying to said area a compound having the formula

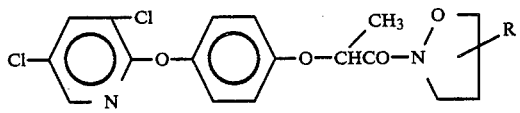

wherein R is hydrogen or $(C_1-C_4)$alkyl at a rate of application of between about 0.01 and about 0.5 pounds of said compound per acre.

2. The method according to claim 1 wherein R is hydrogen or methyl.

3. The method according to claim 2 wherein R is hydrogen.

4. The method according to claim 1 wherein the compound is applied in a composition comprising said compound and an inert diluent at a rate of between 0.01 and about 0.5 pounds of said compound per acre.

5. The method according to claim 4 wherein said compound is applied in a composition comprising said compound and an inert diluent at a rate of between 0.05 and about 0.25 pounds of said compound per acre.

6. The method according to claim 1 wherein the undesirable plants include annual grasses.

7. The method according to claim 6 wherein the undesirable plants include wild oats.

8. The method according to claim 6 wherein the undesirable plants include ryegrass.

9. The method according to claim 6 wherein the undesirable plants include foxtail.

10. The method according to claim 6 wherein the undesirable plants include barnyardgrass.

11. The method according to claim 6 wherein the undesirable plants include signalgrass.

12. The method according to claim 6 wherein the undesirable plants include sprangletop.

13. A method for selectively controlling growth of undesirable monocotyledonous plants in an area containing growing undesirable monocotyledonous plants and an established wheat crop which comprises applying to said area a compound having the formula

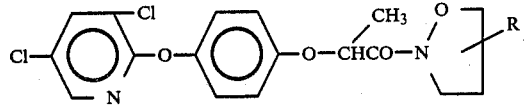

wherein R is hydrogen or $(C_1-C_4)$alkyl at a rate of application of between about 0.01 and about 0.5 pounds of solid compound per acre.

14. A method for selectively controlling growth of undesirable monocotyledonous plants in an area containing growing undesirable monocotyledonous plants and an established rice crop which comprises applying to said area a compound having the formula

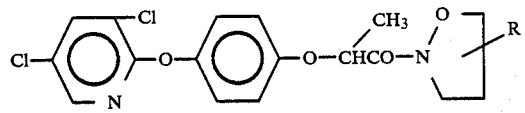

wherein R is hydrogen or $(C_1-C_4)$alkyl at a rate of application of between about 0.01 and about 0.5 pounds of solid compound per acre.

* * * * *

UNITED STATES PATENT AND TRADEMARK OFFICE
CERTIFICATE OF CORRECTION

PATENT NO. : 4,857,101
DATED : August 15, 1989
INVENTOR(S) : Vincent A. Musco, Donald E. Kelley, Carol O. Hansen It is certified that error appears in the above-identified patent and that said Letters Patent is hereby corrected as shown below:

Column 1, line 50: Replace the formula which reads:

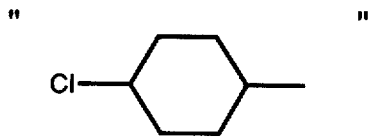

with

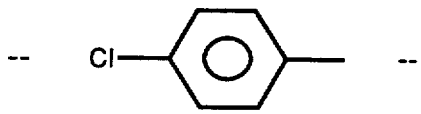

Signed and Sealed this

Nineteenth Day of January, 1993

Attest:

DOUGLAS B. COMER

Attesting Officer      Acting Commissioner of Patents and Trademarks

UNITED STATES PATENT AND TRADEMARK OFFICE
CERTIFICATE OF CORRECTION

PATENT NO. : 4,857,101

DATED : August 15, 1989

INVENTOR(S) : Vincent A. Musco, DonaldE. Kelley, Carl O. Hansen

It is certified that error appears in the above-identified patent and that said Letters Patent is hereby corrected as shown below:

Column 10 (Claim 13), line 47:

Replace "solid" with --said--.

Column 10 (Claim 14), line 62:

Replace "solid" with --said--.

Signed and Sealed this

Fourth Day of January, 1994

*Attest:*

BRUCE LEHMAN

*Attesting Officer*     *Commissioner of Patents and Trademarks*